United States Patent
Choi et al.

(10) Patent No.: US 9,433,596 B2
(45) Date of Patent: Sep. 6, 2016

(54) PHARMACEUTICAL COMPOSITION COMPRISING N-ACETYL-L-CYSTEINE OR ITS DERIVATIVES FOR TREATING ANXIETY DISORDER

(75) Inventors: Suk Woo Choi, Seoul (KR); Suk Won Lee, Seoul (KR); Jeong Yeon Kim, Seoul (KR); Beom Jong Song, Seoul (KR); In Gie Hong, Seoul (KR); Sung Mo Park, Seoul (KR); Ji Hye Kim, Seoul (KR); Jun Uk Lee, Seoul (KR); Bo Bae An, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 341 days.

(21) Appl. No.: 13/820,954

(22) PCT Filed: Sep. 6, 2010

(86) PCT No.: PCT/KR2010/006035
§ 371 (c)(1),
(2), (4) Date: Mar. 5, 2013

(87) PCT Pub. No.: WO2012/033235
PCT Pub. Date: Mar. 15, 2012

(65) Prior Publication Data
US 2013/0172418 A1   Jul. 4, 2013

(51) Int. Cl.
| | | |
|---|---|---|
| A61K 31/198 | (2006.01) |
| A61K 31/195 | (2006.01) |
| A61K 31/355 | (2006.01) |
| A61K 31/51 | (2006.01) |
| A61K 31/525 | (2006.01) |
| A61K 45/06 | (2006.01) |
| A61K 38/05 | (2006.01) |
| A61K 38/17 | (2006.01) |
| A61K 38/18 | (2006.01) |
| A61K 38/21 | (2006.01) |
| A61K 31/18 | (2006.01) |
| A61K 31/216 | (2006.01) |
| A61K 31/55 | (2006.01) |
| A61K 31/5513 | (2006.01) |
| A61K 31/702 | (2006.01) |

(52) U.S. Cl.
CPC ............ *A61K 31/198* (2013.01); *A61K 31/18* (2013.01); *A61K 31/195* (2013.01); *A61K 31/216* (2013.01); *A61K 31/355* (2013.01); *A61K 31/51* (2013.01); *A61K 31/525* (2013.01); *A61K 31/55* (2013.01); *A61K 31/5513* (2013.01); *A61K 31/702* (2013.01); *A61K 38/05* (2013.01); *A61K 38/1709* (2013.01); *A61K 38/1825* (2013.01); *A61K 38/1833* (2013.01); *A61K 38/1866* (2013.01); *A61K 38/21* (2013.01); *A61K 45/06* (2013.01)

(58) Field of Classification Search
CPC .................................................. A61K 31/198
See application file for complete search history.

(56) References Cited

U.S. PATENT DOCUMENTS

2006/0257502 A1  11/2006  Liu
2007/0286909 A1*  12/2007  Smith et al. ................ 424/682

FOREIGN PATENT DOCUMENTS

KR    10-2008-0028357 A    3/2008

OTHER PUBLICATIONS

Marks, "Treatment of Posttraumatic Stress Disorder by Exposure and/or Cognitive Restructuring: A Controlled Study Free", Arch Gen Psychiatry, 1998, 55(4), 317-325 (pp. 1-13).*
Grinberg, et al., "N-acetylcysteine amide, a novel cell-permeating thiol, restores cellular glutathione and protects human red blood cells from oxidative stress", Free Radical Biology & Medicine, vol. 38, pp. 136-145, (2005).
Kim, et al., "Amygdala depotentiation and fear extinction", PNAS, vol. 104, No. 52, pp. 20955-20960, (2007).
Kindt, et al., "Beyond extinction: erasing human fear responses and preventing the return of fear", Nature Neuroscience, vol. 12, No. 3, pp. 256-258, (2009).
Moussawi, et al., "N-Acetylcysteine reverses cocaine-induced metaplasticity", Nature Neuroscience, vol. 12, No. 2, pp. 182-189, (2009).
Ressler, et al., "Cognitive Enhancers as Adjuncts to Psychotherapy: Use of D-Cycloserine in Phobic Individuals to Facilitate Extinction of Fear", Arch Gen Psychiatry, vol. 61, pp. 1136-1144, (2004).
Schiller, et al., "Preventing the return of fear in humans using reconsolidation update mechanisms", Nature, vol. 463, pp. 49-53, (2010).
Zakai, et al., "Synthesis of lipophilic sila derivatives of N-acetylcysteinamide, a cell permeating thiol", Appl. Organometal. Chem., vol. 24, pp. 189-192, (2010).
Sanjay J. Mathew, et al., "Recent Advances in the Neurobiology of Anxiety Disorders: Implications for Novel Therapeutics", Am J Med Genet Part C Semin Med Genet, vol. 148C, pp. 89-98, (2008).

* cited by examiner

*Primary Examiner* — Sahar Javanmard
(74) *Attorney, Agent, or Firm* — Vorys, Sater, Seymour & Pease LLP; Mih Suhn Koh (57) ABSTRACT

The present disclosure relates to a composition for treating anxiety disorder, particularly to a pharmaceutical composition comprising N-acetyl-L-cysteine or its derivatives for treating anxiety disorder such as post traumatic stress disorder or phobia. In accordance with the present disclosure, N-acetyl-L-cysteine can block the renewal of fear memories for a sustained period of time when it was administered during or after an exposure therapy to treat post traumatic stress disorder or phobia.

1 Claim, 6 Drawing Sheets

PHARMACEUTICAL COMPOSITION COMPRISING N-ACETYL-L-CYSTEINE OR ITS DERIVATIVES FOR TREATING ANXIETY DISORDER

CROSS-REFERENCE TO RELATED APPLICATIONS

The present application is a national stage application of International Patent Application No. PCT/KR2010/006035, filed Sep. 6, 2010.

BACKGROUND OF INVENTION

1. Field of the Invention

The present disclosure relates to a composition comprising N-acetyl-L-cysteine or its derivatives for treating anxiety disorder. Particularly the present composition is useful in treating anxiety disorders such as post-traumatic stress disorder and phobia.

2. Description of the Related Art

According to the Epidemiological Survey of Mental Disorders in Korea recently performed on 6,114 people between ages 18 to 64 by Seoul National University and National Mental Hospital, the lifetime prevalence of mental disorder was found to be about 34%. This indicates that one out of every three adults suffers from the illness at least once during their lifetime. Particularly, the survey shows that the lifetime prevalence of anxiety disorder including obsessive-compulsive disorder, post-traumatic stress disorder (PTSD), phobia and the like counts for 6.4% of the total illness.

It has been shown that through a widely used fear conditioning method in animal model, the limbic system such as amygdaloid body and nucleus accumbens are involved in the development of PTSD. Recently it has also been suggested that prefrontal lobe was involved in the return of fear memories (Moussawi et al., 2009, Nat. Neurosci. 12(2):182-9). In addition, it has been shown that the changes in the expression of receptors and the secretion of glutamate in the amygdaloid body and prefrontal lobe play an important role in the maintenance of fear memories. The treatment of PTSD and phobia has been hampered by the return fear memories. The available treatments for PTSD and phobia include cognitive restructuring, group therapy, exposure therapy, selective serotonin reuptake inhibitors (SSRI) and the like. However, they are symptomatic therapy and only temporary. Therefore there are demands for the new therapy.

Among them exposure therapy is a behavior therapy, which involves reliving a traumatic situation or confrontation with a feared object, situation, thought or memory in a controlled and therapeutic environment. It is considered to be one of the most effective treatments for the condition due to its effectiveness in reducing the symptoms of PTSD. However, it has some clinical limitations. Exposure therapy is not permanent and the symptoms return in an unexpected time, place and/or situation. Many researches have been done to prevent the return of fear memories after exposure therapy (Schiller et al., 2010, Nature 463: 49-53; Kindt et al., 2009, Nat. Neurosci. 12(3): 256-8). Further the combined use of a drug together with exposure therapy has been done to improve the efficacy of the therapy and to overcome the limitations (Ressler et al., 2004, Arch. Gen. Psychiatry 61: 1136-44).

Currently there are only limited drugs available to treat anxiety disorder such as PTSD and phobia, the efficacy of which is only marginal and temporary.

SUMMARY OF THE INVENTION

The present disclosure is to provide an effective and long-lasting therapeutic composition to treat anxiety disorder such as PTSD and phobia.

In one aspect, the present disclosure provides a pharmaceutical composition comprising N-acetyl-L-cysteine or its derivatives for treating anxiety disorder.

In one embodiment the present composition may be used to prevent the return f fear memories.

In other embodiment the derivatives includes but are not limited to N-acetyl-L-cysteine amide and its sila derivatives.

In a further embodiment, the present composition may further comprises at least one of supplementary components selected from the group consisting of vitamin, mineral and blood circulation enhancing agents.

In still further embodiment, the anxiety disorder includes, but is not limited to, post-traumatic stress disorder, phobia and panic disorder.

The present composition is administered during or before an exposure therapy to treat the post-traumatic stress disorder and the phobia.

The foregoing summary is illustrative only and is not intended to be in any way limiting. Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

In one aspect, the present disclosure relates to a pharmaceutical composition comprising N-acetyl-L-cysteine (NAC) or its derivatives for treating anxiety disorder.

In one exemplary embodiment, the present composition comprising NAC can prevent the return of fear memoires, which is a serious side effect of exposure therapy, when administered during or after exposure therapy to treat post-traumatic stress disorder and phobia. NAC is known to regulate the concentration of glutamate outside of the nerve cells and receptors on the nerve cells in normal ranges and those effects are suspected to prevent the relapse of fear memory. Therefore, NAC and its derivatives may be useful for treating various anxiety disorder including post-traumatic stress disorder and phobia and the like.

The term "anxiety disorder" as used herein refers to a psychiatric disorder or condition or symptoms where excessive apprehension, uneasiness or fear causes psychological distress or dissociative reaction and includes generalized anxiety disorder, phobia (including specific phobias such as social phobia and agoraphobia, panic disorder, Obsessive-Compulsive Disorder, Post traumatic stress disorder (PTSD) and the like.

The effective component of the present composition is N-acetyl-L-cysteine or its derivatives which includes for example, but is not limited to, N-acetyl-L-cysteine amide (Leonid Grinberg et al., Free Radical Biology & Medicine. 2005, 38, 136-145) or its sila derivatives (Uzma I. Zakai et al., 2010, Appl. Organometal. Chem. 24: 189-192). In one exemplary embodiment of the present disclosure, the preferred component is N-acetyl-L-cysteine.

N-acetyl-L-cysteine (NAC) is a precursor of an amino acid L-cysteine. Also, NAC is a precursor of glutathione which is an antioxidant that removes toxins from the liver. Further NAC has been shown to slow down the replication of Human Immunodeficiency virus, and to protect cells from the damage caused by chemotherapy, radio therapy and others drugs. NAC has been commercialized as medicine or health supplements due to its therapeutic effects on bronchitis, asthma, pneumonia and cystic fibrosis where NAC has been shown to clear the mucus. NAC is a weak acid having pKa of 3.24 and usually formulated as a tablet with calcium stearate.

Also, the present composition may further comprise at least one of supplemental components such as vitamins, minerals and blood circulation enhancing agents.

The example of vitamins which may be included in the present composition includes, but is not limited to, vitamins B1, B2, B6, B12, and C, pantothenate calcium, nicotinamide, folic acid and biotin and the like.

The example of minerals which may be included in the present composition includes, but is not limited to, zinc, iron, calcium, and magnesium.

The combined use of vitamins and minerals together with the present composition is beneficial because it complements the bioactivity. The vitamins and minerals may be included in the composition at the concentration of about 0.1 to 10% by weight of the total. Particularly, vitamins B1, B2, or C are included in the composition at the final concentration of about 0.01 to 3% by weight, about 0.01 to 3% by weight and 0.01 to 4% by weight of the total, respectively.

The exemplary blood circulation enhancing agents that may be used for the present composition include, but are not limited to, gamma linoleic acid, EPA, and tocopherol and the like.

The blood circulation enhancing agents used with the present composition stimulates the blood circulation and complements the bioactivity. The preferred blood circulation agent is tocopherol, which may be included in the composition at the final concentration of about 5 to 30% by weight.

The present pharmaceutical composition can be administered by conventional methods known in the related art. The preferred routes of administration include intravenous, peritoneal, subcutaneous, intradermal, intranodal, muscular, transdermal, inhalation, intranasal, oral, intraocular, intraarticular, intraspinal, and intracephalic delivery.

The present pharmaceutical composition can be formulated into granules, tablets, capsules, suspension, emulsion, syrup, or aerosol for oral administration, sterilized injection fluid, suppository or can be formulated for transdermal delivery. The examples of carriers, excipients or diluents which can be used for the present composition include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, ethyl alcohol, methylhydroxy benzoate, propylhydroxybenzoate, talc, magnesium stearate and mineral oil.

In one embodiment, the present pharmaceutical composition may be formulated into solid preparations for oral use. The solid preparations for oral delivery include tablets, granules, capsules, pills and powder. The solid preparations can be formulated with at least one excipient such as starch, calcium carbonate, sucrose, lactose or gelatin with the present effective ingredient. Or lubricants such as magnesium stearate, talc may also be used.

In other aspect, the present composition may be formulated into liquid preparations for oral use. The liquid preparations for oral delivery include suspension, liquid for internal use, emulsion, and syrups and the like. Also conventionally included in the preparations are inactive diluents (for example purified water, ethanol, liquid paraffin) and variety of excipients, for example, wetting agents, sweetening agents, odorants, and preservatives.

In other aspects, the present composition may be formulated into parenteral preparations particularly for peritoneal administration. The parenteral preparations include sterilized aqueous solution, non-aqueous solvent, suspension, emulsion, freeze dried preparations and suppository. The sterilized aqueous solution includes Hank's solution, Ringer's solutions or suitable buffer solutions such as buffered salt solutions. The non-aqueous solvents include propylene glycol, polyethylene glycol, vegetable oils such as olive oil, injectable ester such as ethyl oleate. Preservatives, stabilizing agents, wetting agents, emulsifying agents, salts for regulating osmotic pressure and/or buffering agents may also be used if desired. The suppository preparation may include conventional bases such as Witepsol®, macrogol (polyethylene glycol), Tween® 61, cacao butter, Sevum Laurinum, or glycerogelatin.

The present composition formulated as described above may be administered in an effective amount via various routes including parenteral or non-parenteral methods. The term "effective amount" as used herein refers to the amount of a compound sufficient to result in the prevention or treatment of disorders or symptoms of interest.

The dosage may vary, and the optimal amount may be selected in consideration of administration routes used, age, sex, body weight, medical condition and/or other personal differences of the subject. Various amounts of the effective ingredient may be used depending on the severity of the disease, and may be administered as 1~1000 mg/kg of body weight/day, particularly 10~500 mg/kg of body weight/day, more particularly 100~200 mg/kg of body weight/day.

The present composition, when it is combined with exposure therapy to treat PTSD or phobia, may be administered during, before and/or after the exposure therapy.

In accordance of the present disclosure, N-acetyl-L-cysteine was able to prevent the return of fear memories which is the severe side effects of exposure therapy to treat PTSD and phobia, particularly when NAC was administered during or after the exposure therapy.

Without being bound by the theory, it is presumed that NAC exerts its effects by regulating the concentration of glutamate at the normal level outside nerve cells and various receptors of nerve cells which are involved in the return of fear memories. Therefore, NAC or its derivatives can be used beneficially to treat anxiety disorders such as PTSD and phobia.

NAC, which has been approved by FDA, can be orally administered and penetrate a blood-brain barrier. Thus immediate clinical use is possible upon the demonstration of therapeutic effects of NAC on treating anxiety disorders such as PTSD and phobia The present disclosure is further explained in more detail with reference to the following examples. These examples, however, should not be interpreted as limiting the scope of the present invention in any manner.

EXAMPLES

Example 1

Prevention of Renewal of Memory During an Exposure Therapy by the Administration of NAC The following experiments were performed to test the effect NAC on blocking the return of fear memories in exposure therapy to reduce the fear memories.

Example 1-1

Fear Conditioning and Extinction Training

All procedures were approved by the Institute of Laboratory Animal Resources of Seoul National University. Sprague-Dawley Rats (8-9 weeks old, from Samtaco, Korea) were maintained with free access to water and food with 12 hour dark/light cycles (lights off at 09:00 hrs). Group of three to six animals were used for each experiment. (26 in total)

For fear conditioning, the rats were presented with a tone (2.8 kHz, 85 dB) co-terminating with an electrical shock (1.0 mA, 1 s) three times at an interval of 100 sec.

The rats were returned to the cage 1 minute after the last shock has been applied. Three days after the conditioning, the exposure therapy was done in a chamber distinct from the conditioning chamber for both extinction training and tone tests. 10 tones were presented at an interval of 100 sec without shocks, during which the freezing responses were measured to determine the reduction of fear memories. Unpaired, two-tailed T-test was used to analyze the results.

Example 1-2

Administration of NAC

Figure 1:
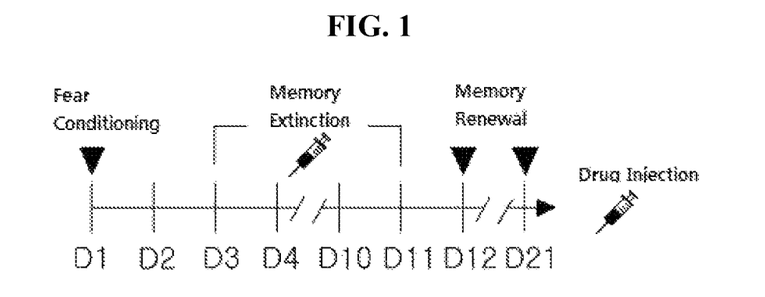
FIG. 1 is an exemplary schematic representation of the experimental design to administer N-Acetyl-L-cysteine during the fear memory extinction process.

In the Example 1-1, from 3 to 5 days after the conditioning, NAC in physiological saline was peritoneally administered once a day at the concentration of 200 mg/kg, 2.5 hours before the exposure therapy was applied. The negative control was only received physiological saline. The scheme is shown in FIG. 1.

Example 1-3

Fear Memory Renewal Test

The renewal test was done on day 12 after the conditioning was completed. The same chamber and place as it was used for the fear conditioning were used for the renewal. The rats with the extinction training were placed in the conditioning chamber and were left undisturbed for 10 minutes. Then the fear memory was recalled by presenting the rats with a tone for 30 sec. The fear memory recalled was determined by measuring the freezing response as described before (Kim et al., 2007, PNAS 104 (52): 20955-960). The freezing was defined as immobility except for respiratory movements and was quantified by trained observers who were blind to the experimental groups.

Figure 2:
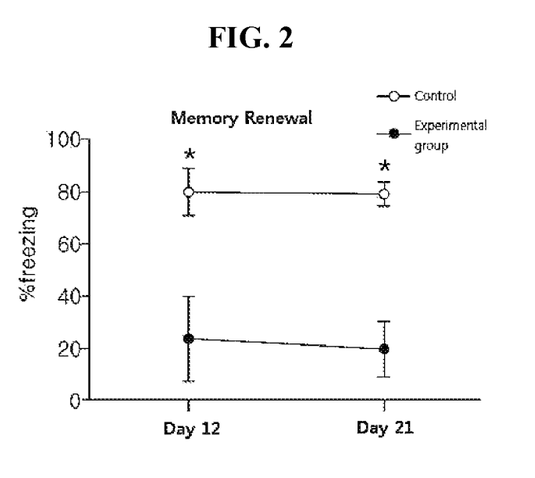
FIG. 2 is a graph showing the effect of N-Acetyl-L-cysteine administered during the fear memory extinction process. The result indicates that the return of fear-memories was prevented and the effect was long-lasted.

To test the sustained effects of the drug used, additional renewal test was performed on day 21 after the fear conditioning test was completed. As shown in FIG. 2, the renewal of the fear memory was blocked in the experimental groups that received NAC in contrast to the control group.

Example 2

Figure 3:
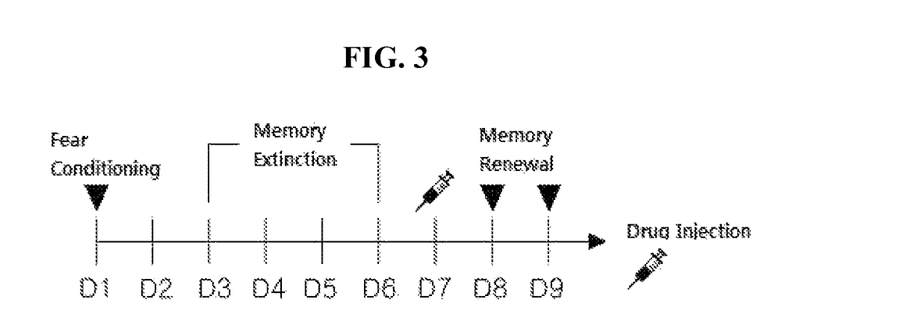
FIG. 3 is an exemplary schematic representation of the experimental design to determine the effect of N-Acetyl-L-cysteine administered after the fear memory extinction process, in which the fear memories were renewed one day after the administration of N-Acetyl-L-cysteine.
Figure 4:
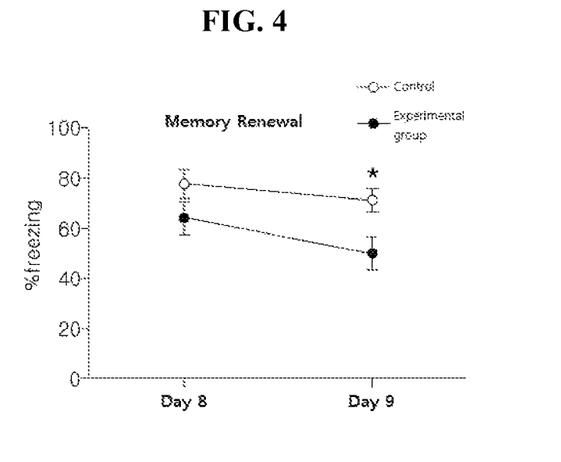
FIG. 4 is a graph showing the effect of N-Acetyl-L-cysteine administered after the fear memory extinction process and before the renewal of fear memories. The result indicates that the return of fear-memories was prevented in the rats tested.

The Blockade of Fear Memories by the Administration of NAC One Day Before a Renewal Test The same procedures as described in Example 1-1 were used for the conditioning and extinction training. The extinction training was performed for 4 days starting from day 3 after the conditioning was applied. On the 7th day, 200 mg/kg of NAC was injected peritoneally. On the 8 and 9th day after the completion of the conditioning, the renewal test was performed to measure the response to fear as described in Example 1-3 (See FIG. 3). As shown in FIG. 4, on the 9 th day after the fear conditioning, the renewal of the fear memory was blocked in the experimental groups that received NAC in contrast to the control group.

Example 3

Figure 5:
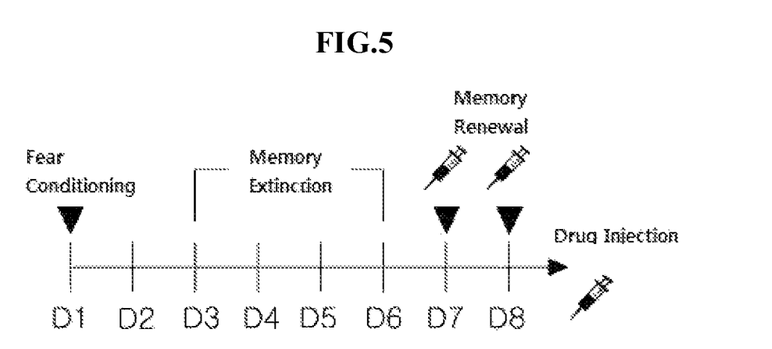
FIG. 5 is an exemplary schematic representation of the experimental design to determine the extent to which the return is prevented by the administration of N-Acetyl-L-cysteine that was administered immediately before the renewal of fear memories.
Figure 6:
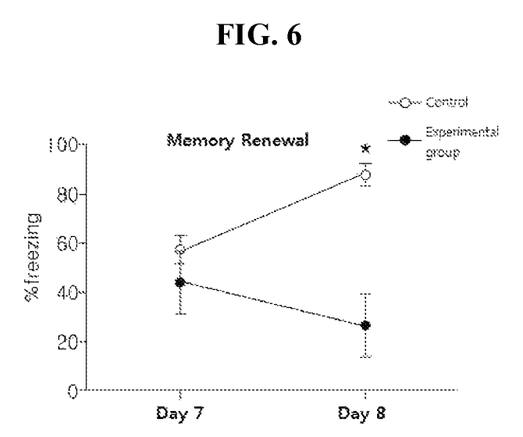
FIG. 6 is a graph showing that the N-Acetyl-L-cysteine administered immediately before the renewal of fear memories prevented the return of fear-memories in the rats tested.

The Prevention of Fear Memories by the Administration of NAC Immediately Before a Renewal Test The same procedures as described in Example 1-1 were used for the conditioning and extinction training. The extinction training was performed for 4 days starting from the day 3 after the conditioning was applied. On the 7th and 8th day after the completion of the conditioning, at 2.5 hours before the renewal test was started, 200 mg/kg of NAC was injected peritoneally. The renewal test was performed as described in Example 1-3 (See FIG. 5). As shown in FIG. 6, on the 8th day after the fear conditioning, the renewal of the fear memory was blocked in the experimental groups received NAC in contrast to the control group.

In accordance with the present disclosure, NAC and its derivatives is utilized as pharmaceutical composition for treating anxiety disorder including PTSD or phobia.

What is claimed is:
1. A method for preventing a relapse of fear memories in a post-traumatic stress disorder or phobia comprising administering to a subject who is treated with an exposure therapy a composition comprising an effective amount of N-acetyl-

L-cysteine, N-acetyl-L-cysteine amide or a sila-amide form of N-acetyl-L-cysteine as a single active ingredient.

\* \* \* \* \*